(12) United States Patent
Meng et al.

(10) Patent No.: US 8,372,046 B2
(45) Date of Patent: Feb. 12, 2013

(54) DRUG DELIVERY DEVICE WITH IN-PLANE BANDPASS REGULATION CHECK VALVE IN HEAT-SHRINK PACKAGING

(75) Inventors: Ellis Meng, Pasadena, CA (US); Ronalee Lo Mann, Somerville, MA (US)

(73) Assignee: University of Southern California, Los Angeles, CA (US)

( * ) Notice: Subject to any disclaimer, the term of this patent is extended or adjusted under 35 U.S.C. 154(b) by 340 days.

(21) Appl. No.: 12/709,188

(22) Filed: Feb. 19, 2010

(65) Prior Publication Data

US 2010/0217209 A1 Aug. 26, 2010

Related U.S. Application Data

(60) Provisional application No. 61/154,314, filed on Feb. 20, 2009, provisional application No. 61/266,978, filed on Dec. 4, 2009, provisional application No. 61/266,977, filed on Dec. 4, 2009.

(51) Int. Cl.
*A61M 5/00* (2006.01)

(52) U.S. Cl. ...................................... 604/246

(58) Field of Classification Search .................. 604/6.1, 604/9, 34, 99.04, 237, 247, 236, 246; 251/5, 251/63.5, 82, 147, 149.8, 314
See application file for complete search history.

(56) References Cited

U.S. PATENT DOCUMENTS

| | | | | |
|---|---|---|---|---|
| 2,497,906 A | * | 2/1950 | Peters et al. | 137/496 |
| 4,699,615 A | | 10/1987 | Fischell et al. | |
| 4,712,583 A | * | 12/1987 | Pelmulder et al. | 137/852 |
| 4,919,167 A | * | 4/1990 | Manska | 137/512 |
| 4,946,448 A | * | 8/1990 | Richmond | 604/247 |
| 5,025,829 A | * | 6/1991 | Edwards et al. | 137/512 |
| 5,090,963 A | | 2/1992 | Gross et al. | |
| 5,135,499 A | | 8/1992 | Tafani et al. | |
| 5,318,557 A | | 6/1994 | Gross | |
| 5,472,122 A | * | 12/1995 | Appleby | 222/212 |
| 5,771,935 A | * | 6/1998 | Myers | 137/859 |
| 5,775,671 A | * | 7/1998 | Cote, Sr. | 251/149.8 |
| 5,906,597 A | * | 5/1999 | McPhee | 604/246 |

(Continued)

FOREIGN PATENT DOCUMENTS

WO 0166173 A1 9/2001

OTHER PUBLICATIONS

International Search Report and Written Opinion of the International Searching Authority (Korean Intellectual Property Office), mailed Oct. 19, 2010, for PCT Application No. PCT/US2010/024730, filed Feb. 19, 2010 (international application corresponding to U.S. Appl. No. 12/709,188).

(Continued)

*Primary Examiner* — Nicholas Lucchesi
*Assistant Examiner* — Diva K Chander
(74) *Attorney, Agent, or Firm* — McDermott Will & Emery LLP

(57) ABSTRACT

A drug delivery device may include a drug reservoir configured to contain and controllably deliver a fluidic drug. A tube may be configured to deliver the fluid from the drug reservoir through a lumen in the tube to another location. A valve wholly within the lumen of the tube may regulate the flow of the fluid through the tube without substantially diverting the direction in which the fluid flows through the tube. The valve may contain only a single member which moves during operation of the valve. The valve may be configured to regulate the flow of fluid in a bandpass manner by allowing fluid to flow through the valve only when the pressure of the fluid is above a minimum and below a maximum. The valve may be held in place within the tube solely by frictional force between the valve and a wall of the tube.

21 Claims, 11 Drawing Sheets

| | Valve Seat/ Pressure Limiter | Hole Valve Plate | Arm Valve Plate | S-Shape Valve Plate | Spacer Plate |
|---|---|---|---|---|---|
| Material | SU-8 | MDX4-4210 | MDX4-4210 | MDX4-4210 | SU-8 |
| Diameter [µm] | 900 | 900 | 900 | 900 | 900 |
| Thickness [µm] | 180 | 75 | 75 | 75 | 40 |

U.S. PATENT DOCUMENTS

| | | | | |
|---|---|---|---|---|
| 6,079,449 | A | * | 6/2000 | Gerber .......................... 137/859 |
| 6,089,272 | A | * | 7/2000 | Brand et al. ................... 137/859 |
| 6,960,192 | B1 | | 11/2005 | Flaherty et al. |
| 7,771,176 | B2 | * | 8/2010 | Weber ........................ 417/410.2 |
| 2001/0025160 | A1 | * | 9/2001 | Felix et al. .................... 604/183 |
| 2003/0229310 | A1 | | 12/2003 | Flaherty et al. |
| 2004/0054333 | A1 | | 3/2004 | Theeuwes et al. |
| 2004/0068224 | A1 | | 4/2004 | Couvillon et al. |
| 2005/0013805 | A1 | | 1/2005 | Tavori |
| 2008/0039792 | A1 | | 2/2008 | Meng et al. |
| 2008/0086095 | A1 | * | 4/2008 | Dikeman et al. .............. 604/247 |
| 2008/0230053 | A1 | | 9/2008 | Kraft et al. |
| 2008/0255500 | A1 | | 10/2008 | Kissinger et al. |
| 2009/0071137 | A1 | * | 3/2009 | Harris ............................ 60/325 |
| 2010/0222769 | A1 | | 9/2010 | Meng et al. |

OTHER PUBLICATIONS

Bohm, S. et al. 2000. A closed-loop controlled electrochemically actuated micro-dosing system. Journal of Micromechanics and Microengineering, vol. 10, No. 4, 2000, pp. 498-504.

Feng, G.-H. et al. 2003. Universal concept for fabricating micron to millimeter sized 3-D parylene structures on rigid and flexible substrates, Technical Digest of the 16th IEEE International Conference on Micro Electro Mechanical Systems (MEMS 2003), Kyoto, Japan, Jan. 19-23, 2003, pp. 594-597.

Kang, H.-W. et al. 2006. Development of a micro-bellows actuator using micro-stereolithography technology. Microelectronic Engineering, vol. 83, No. 4-9, 2006, pp. 1201-1204.

Li, P.-Y. et al. 2009. A Parylene Bellows Electrochemical Actuator for Intraocular Drug Delivery. Transducers 2009, Denver, Colorado, USA, Jun. 21-25, 2009, pp. 1461-1464.

Li, P.-Y. et al. 2010. A Parylene Bellows Electrochemical Actuator. IEEE/ASME Journal of Microelectromechanical Systems, vol. 19, No. 1, 2010, pp. 215-228.

Luharuka, R. et al. 2004. Design, fabrication, and testing of a near constant pressure fuel delivery system for miniature fuel cells. Sensors and Actuators A: Physical, vol. 112, No. 2-3, 2004, pp. 187-195.

Metref, L. et al. 2007. Contactless Electrochemical Actuator for Microfluidic Dosing. IEEE/ASME Journal of Microelectromechanical Systems, vol. 16, No. 4, 2007, pp. 885-892.

Neagu, C. R. et al. 1996. An electrochemical microactuator: Principle and first results. IEEE/ASME Journal of Microelectromechanical Systems, vol. 5, No. 1, 1996, pp. 2-9.

O'Keefe, D. et al. 1994. Patient-controlled analgesia using a miniature electrochemically driven infusion pump. British Journal of Anaesthesia, vol. 73, No. 6, 1994, pp. 843-846.

Pang, C. et al. 2006. Electrolysis-based diaphragm actuators. Nanotechnology, vol. 17, No. 4, 2006, pp. S64-S68.

Stanczyk, T. et al. 2000. A microfabricated electrochemical actuator for large displacements. IEEE/ASME Journal of Microelectromechanical Systems, vol. 9, No. 3, 2000, pp. 314-320.

Xie, J. et al. 2004. An electrochemical pumping system for on-chip gradient generation. Analytical Chemistry, vol. 76, No. 13, 2004, pp. 3756-3763.

Yang, X. et al. 1997. Micro bellow actuators, Proceedings of International Conference on Solid-State Sensors and Actuators (Transducers 97), Chicago, IL, USA, Jun. 16-19, 1997, pp. 45-48.

Yuan, G. et al. 2005. Kinematically-stabilized microbubble actuator arrays, Technical Digest of the 18th IEEE International Conference on Micro Electro Mechanical Systems (MEMS 2005), Miami, FL, USA, Jan. 30-Feb. 3, 2005, pp. 411-414.

International Search Report and Written Opinion of the International Searching Authority (Korean Intellectual Property Office), mailed Jan. 18, 2011, for PCT Application No. PCT/US2010/024808, filed Feb. 19, 2010 (international application corresponding to U.S. Appl. No. 12/709,335).

Chen, P.-J. et al. 2006. Surface-Micromachined In-Channel Parylene Dual Valves for Unpowered Microflow Regulation. Hilton Head 2006: A Solid State Sensors, Actuators and Microsystems Workshop, Hilton Head Island, South Carolina, USA, Jun. 4-8, 2006, pp. 205-208.

Chen, P.-J. et al. 2007. Surface-Micromachined Parylene Dual Valves for On-Chip Unpowered Microflow Regulation. IEEE/ASME Journal of Microelectromechanical Systems, vol. 16, No. 2, 2007, pp. 223-231.

Chen, P.-J. et al. 2008. Floating-Disk Parylene Microwave for Self-Regulating Biomedical Flow Controls, Technical Digest of the 20th IEEE International Conference on Micro Electro Mechanical Systems (MEMS 2008), Tucson, AZ, USA, Jan. 13-17, 2008, pp. 575-578.

Gensler, H. et al. 2010. Implantable MEMS Drug Delivery Devices for Cancer Radiation Reduction. MEMS 2010, Hong Kong, China, Jan. 24-28, 2010, pp. 23-26.

Givrad, T.K. et al. 2008 Implantable Minipump with MEMS Electrothermal Valve for Bolus Injection in Mice. Frontiers in Biomedical Devices, Irvine, California, USA, Jun. 18-20, 2008, BioMed2008.

Li, P.-Y. et al. 2007. An Electrochemical Intraocular Drug Delivery Device. MEMS 2007, Kobe, Japan, Jan. 21-25, 2007 pp. 15-18.

Li, P.-Y. et al. 2007. Surgical Testing of a Microelectromechanical Systems (MEMS) Ocular Drug Delivery System. BMES Annual Fall Meeting, Los Angeles, California, USA, Sep. 26-29, 2007. Abstract only.

Li, P.-Y. et al. 2008. Parylene Electrothermal MEMS Drug Delivery Valve. Spring Annual Meeting of the American Chamical Society: Progress in Vapor-Born Poly (p-xylylene)s, Preparation, Properties, Application, New Orleans, Louisiana, USA, Apr. 6-10, 2008, pp. 941-942.

Li, P.-Y. et al. 2008. An Electrochemical Intraocular Drug Delivery Device. Sensors and Actuators A: Physical, vol. 143, Issue 1, 2008, pp. 41-48.

Li, P.-Y. et al. 2008 A Wirelessly-Activated Parylene Electrothermal Valve for Mapping Brain Function in Freely Moving Subjects. Hilton Head 2008: A Solid State Sensors, Actuators and Microsystems Workshop, Hilton Head Island, South Carolina, USA, Jun. 1-5, 2008, pp. 32-35.

Li, P.-Y. et al. 2008. Mechanical and Thermal Modeling of a Parylene Electrothermal Valve for Mapping Brain Function in Freely Moving Subjects. μTAS 2008, Twelfth International Conference on Miniaturized Systems for Chemistry and Life Sciences, San Diego, California, USA, Oct. 12-16, 2008, pp. 1105-1107.

Li, P.-Y. et al. 2008. Parylene Electrothermal Valve for Rapid in Vivo Drug Delivery. American Vacuum Society Topical Workshop on BioMEMS, Boston, Massachusetts, USA, Oct. 19-24, 2008. Abstract only.

Li, P.-Y. et al. 2009. A Parylene MEMS Electrothermal Valve. IEEE/ASME Journal of Microelectromechanical Systems, vol. 18, No. 6, 2009, pp. 1184-1197.

Li, P.-Y. et al. 2010. A Low Power, On Demand Electrothermal Valve for Wireless Drug Delivery Applications. Lab on a Chip, vol. 10, Issue 1, 2010, pp. 101-110.

Lin, J. C.-H. et al. 2009. Minimally Invasive Parylene Dual-Valved Flow Drainage Shunt for Glaucoma Implant, Technical Digest of the 22nd IEEE International Conference on Micro Electro Mechanical Systems (MEMS 2009), Sorrento, Italy, Jan. 25-29, 2009, pp. 196-199.

Lo, R. et al. 2006. A Passive Refillable Intraocular MEMS Drug Delivery Device. IEEE Engineering in Medicine and Biology Society Special Topic Conference on Microtechnologies in Medicine and Biology, Okinawa, Japan, May 9-12, 2006, pp. 74-77.

Lo, R. et al. 2007. Refillable MEMS Drug Delivery Pump for Chronic Ocular Disease. ARVO 2007, Ft. Lauderdale, Florida, USA, May 6-10, 2007. Abstract only.

Lo, R. et al. 2008. In Vivo Studies Demonstrating Feasibility and Biocompatibility of a MEMS Ocular Drug Delivery System. BMES Annual Fall Meeting, St. Louis, Missouri, USA, Oct. 2-4, 2008. Abstract only.

Lo, R. et al. 2009. In-Plane Bandpass Regulation Check Valve in Heat-Shrink Packaging for Drug Delivery. MEMS 2009, Sorrento, Italy, Jan. 25-29, 2009, pp. 236-239.

Lo, R. et al. 2009. A Passive MEMS Drug Delivery Pump for Treatment of Ocular Diseases. Biomedical Microdevices, vol. 11, No. 5, 2009, pp. 959-970.

Meng, E. 2009. Implantable Microfluidic Delivery Platforms for Chronic Administration of Agents for Scientific Discovery and Therapy. Illuminating the Genetic Architecture of Common Eye Disease, Avalon, California, USA, Feb. 3-7, 2009. Abstract only.

Meng, E. 2009. Implantable Microfluidic Delivery Platforms for Chronic Administration of Agents for Scientific Discovery and Therapy. AALAS National Meeting, Denver, Colorado, USA, Nov. 8-12, 2009. Abstract only.

Meng, E. et al. 2000. A Check-Valved Silicone Diaphragm Pump, MEMS 2000, Miyazaki, Japan, Jan. 23-27, 2000, pp. 62-67.

Meng, E. et al. 2006. Electrolysis-Driven Drug Delivery for Treatment of Ocular Disease. µTAS 2006, 10th International Conference on Miniaturized Systems for Chemistry and Life Sciences, Tokyo, Japan, Nov. 5-9, 2006, pp. 633-635.

Meng, E. et al. 2008. Implantable MEMS Drug Delivery Systems for Administration of Unaltered Therapeutic Agents. USC Translational Nanoscience Conference: Re-Engineering Basic and Clinical Research to Catalyze Translational Nanoscience, Los Angeles, California, USA, Mar. 20-21, 2008. Abstract only.

Meng, E. et al. 2009. Implantable MEMS Drug Delivery Pumps for Small Animal Research. 31st IEEE Engineering in Medicine and Biology Conference, Minneapolis, Minnesota, Sep. 2-6, 2009, pp. 6696-6698.

Pan, T. et al. 2006. A Reworkable Adhesive-Free Interconnection Technology for Microfluidic Systems. IEEE/ASME Journal of Microelectromechanical Systems, vol. 15, No. 1, 2006, pp. 267-272.

Pan, T. et al. 2006. An Artificial Nano-Drainage Implant (ANDI) for Glaucoma Treatment. 28th Annual International Conference of the IEEE Engineering in Medicine and Biology Society, EMBS '06., New York, NY, Aug. 30-Sep. 3, 2006, pp. 3174-3177.

Saati, S. et al. 2007. Surgical Methods to Place a Novel Refillable Ocular Microelectromechanical System (MEMS) Drug Delivery Device. ARVO 2007, Ft. Lauderdale, Florida, USA, May 6-10, 2007. Abstract only.

Saati, S. et al. 2008. Surgical Methods to Place a Novel Refillable Ocular Microelectromechanical System (MEMS) Drug Delivery Device. ARVO 2008, Ft. Lauderdale, Florida, USA, Apr. 27-May 1, 2008. Abstract only.

Saati, S. et al. 2009. Mini Drug Pump for Ophthalmic Use. American Ophthalmological Society, 145th Annual Meeting, Half Moon Bay, California, USA, May 14-17, 2009. Abstract only.

Saati, S. et al. 2009. Mini Drug Pump for Ophthalmic Use. Transactions of the American Ophthalmological Society, vol. 107, 2009, pp. 60-71.

Saati, S. et al. 2010. Mini Drug Pump for Ophthalmic Use. Current Eye Research, vol. 35, No. 3, 2010, pp. 192-201.

Wang, X.-Q. et al. 2000. A Normally Closed In-Channel Micro Check Valve, Technical Digest of the 14th IEEE International Conference on Micro Electro Mechanical Systems (MEMS 2000), Miyazaki, Japan, Jan. 23-27, 2000, pp. 68-73.

Xie, J. et al. 2001. Surface Micromachined Leakage Proof Parylene Check Valve, Technical Digest of the 14th IEEE International Conference on Micro Electro Mechanical Systems (MEMS 2001), Interlaken, Switzerland, Jan. 21-25, 2001, pp. 539-542.

Lo, R. et al. 2008. A Refillable Microfabricated Drug Delivery Device for Treatment of Ocular Diseases. Lab on a Chip, vol. 8, Issue 7: pp. 1027-1030.

Whalen, J. et al. 2005. Electrochemical Deposition of Platinum from Aqueous Ammonium Hexachloroplatinate Solution. Journal of the Electrochemical Society, vol. 152: pp. C738-C743.

* cited by examiner

| | Valve Seat/ Pressure Limiter | Hole Valve Plate | Arm Valve Plate | S-Shape Valve Plate | Spacer Plate |
|---|---|---|---|---|---|
| Material | SU-8 | MDX4-4210 | MDX4-4210 | MDX4-4210 | SU-8 |
| Diameter [μm] | 900 | 900 | 900 | 900 | 900 |
| Thickness [μm] | 180 | 75 | 75 | 75 | 40 |

Membrane Only          Membrane & Bossed Structure          Membrane, Bossed & Overlap ―100μm  ―100μm  ―100μm  ―100μm Assemble valve on jig | Put heat shrink around valve | Place setup in oven 200 °C | Remove setup from jig

DRUG DELIVERY DEVICE WITH IN-PLANE BANDPASS REGULATION CHECK VALVE IN HEAT-SHRINK PACKAGING

CROSS-REFERENCE TO RELATED APPLICATIONS

This application is based upon and claims priority to U.S. Provisional Patent Application No. 60/154,314, entitled "IN-PLANE BANDPASS REGULATION CHECK VALVE IN HEAT-SHRINK PACKAGING FOR DRUG DELIVERY," filed Feb. 20, 2009, U.S. Provisional Patent Application No. 61/266,978, entitled "ELECTROCHEMICAL BELLOWS FLUID DOSING DEVICE," filed Dec. 4, 2009, and U.S. Provisional Patent Application No. 61/266,977, entitled "RADIATION-DOSE REDUCTION USING siRNA NANOPARTICLE DELIVERY VIA MEMS-BASED PUMPS," filed Dec. 4, 2009.

This application is also related to U.S. Provisional Patent Application 61/154,327, entitled "MEMS ELECTROCHEMICAL BELLOWS ACTUATOR," filed Feb. 20, 2009, and U.S. patent application Ser. No. 12/709,335, entitled "MEMS ELECTROCHEMICAL BELLOWS ACTUATOR," which is being filed on the same day as this application.

The entire content of all of these applications is incorporated herein by reference.

STATEMENT REGARDING FEDERALLY SPONSORED RESEARCH

This invention was made with Government support under Contract No. R21EY018490 awarded by the National Institutes of Health (NIH), and Contract No. EEC-0310723 awarded by the National Science Foundation (NSF). The Government has certain rights in the invention.

BACKGROUND

1. Technical Field

This disclosure relates to micro electro mechanical systems (MEMS), including micro electro mechanical valves and related drug delivery devices.

2. Description of Related Art

Drug delivery devices have been fitted with a MEMS check valve oriented out-of-plane. See, e.g., Ronalee Lo, Po-Ying Li, Saloomeh Saati, Rajat Agrawal, Mark S. Humayun, and Ellis Meng, *A Passive Refillable Intraocular MEMS Drug Delivery Device*. Lab on a Chip, Vol. 8, Issue 7, 2008, pp. 1027-1030.

However, devices of this type may lack over-pressure protection and thus permit accidental dosing. The out-of-plane orientation of the valve may also interfere with in vivo operation due to contact with tissues.

SUMMARY

A drug delivery device may include a drug reservoir configured to contain and controllably deliver a fluidic drug. A tube may be configured to deliver the fluid from the drug reservoir through a lumen in the tube to another location. A valve wholly within the lumen of the tube may regulate the flow of the fluid through the tube without substantially diverting the direction in which the fluid flows through the tube.

The valve may be configured to regulate the flow of fluid in a bandpass manner by allowing fluid to flow through the valve only when the pressure of the fluid is above a minimum and below a maximum.

The valve may contain only a single member which moves during operation of the valve.

The valve may be held in place within the tube solely by frictional force between the valve and a wall of the tube.

The valve may include a valve seat and a flexible valve plate configured to rest against the valve seat, both of which may contain at least one fluid-communication channel in line with the lumen of the tube.

The valve plate may include a plurality of fluid-communication channels in line with the lumen of the tube. Each fluid-communication channel in the valve plate may have a cross section that is substantially circular, S-shaped, or polygonal.

The valve may include a pressure limiter, a flexible valve plate between the pressure limiter and the valve seat, and a spacer plate between the flexible valve plate and the valve seat.

The pressure limiter and the valve seat may each include two or more separated annular protrusions.

The valve may be configured such that only the valve plate moves during operation of the valve.

The valve may include a stack of disk-like components held together solely by frictional force. The frictional force may be the result of shrinkage of the tube wall surrounding the valve after the valve is placed within the lumen of the tube. The shrinkage may be caused by application of heat to the tube. The frictional force may be the result of the valve being press fitted within the lumen of the tube.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it refers to the same or like components or steps.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

A check valve may provide dual regulation of in-plane flow. Heat-shrink tubing packaging may also be used. This modular design may be optimized for integration into low-profile fluidic devices requiring flow control, such as drug delivery devices. The device may be implanted within the eye. Theoretical and finite-element-modeling (FEM) analyses may be performed to guide valve design and may be confirmed experimentally. The valve may allow flow between 150-900 mmHg (20-120 kPa) and may withstand >500 mmHg (66.7 kPa) of reverse pressure. This packaging scheme may not require adhesives and may be extremely robust (>2000 mmHg without leakage).

Figure 1:
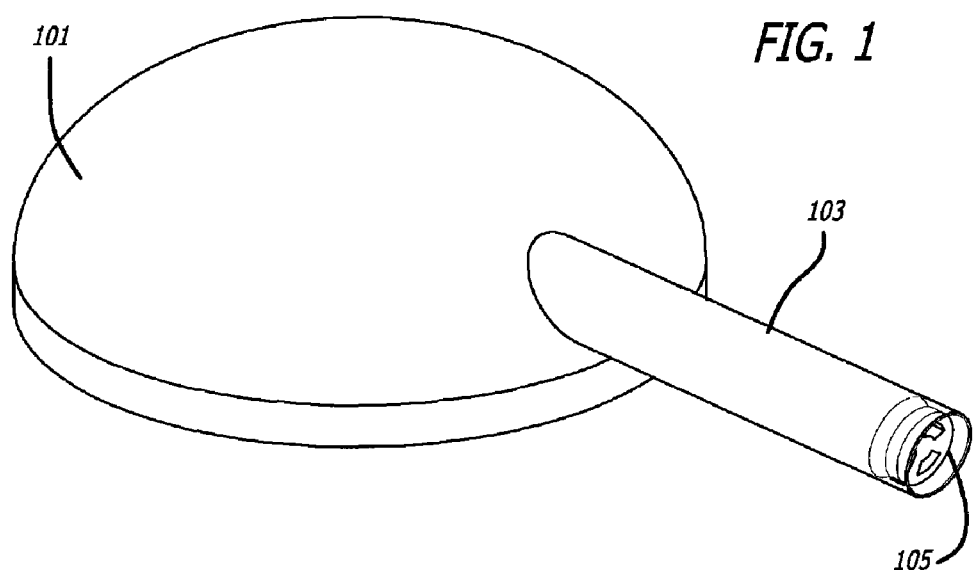
FIG. 1 illustrates a surgical model for a MEMS drug delivery device.

FIG. 1 illustrates a surgical model for a MEMS ocular drug delivery device. The drug delivery device may include a drug reservoir 101, a biocompatible heat-shrink tube 103, and a valve 105 in line with the tube 103. The diameter of the interior lumen of the tube 103 and the corresponding cross-section of the valve 105 may be no greater than 1 mm.

The drug reservoir 101 may be configured to contain a fluidic drug and to controllably deliver this drug through the tube 103 under the regulation of the valve 105. The drug reservoir 101 may be configured as set forth in any of the co-pending applications identified above in the Cross-Reference to Related Applications section. The drug delivery device may be surgically implanted within a living organism, such as within an eye or elsewhere within a human being.

Device shape and component placement may be optimized for safety and efficacy. The valve 105 may be suitable for other microfluidic flow regulation applications. Other shapes may be accommodated by selecting heat shrink tubing with appropriate initial and final dimensions. Although only a single tube and valve are depicted in FIG. 1, multiple individual tube and valve units may be configured to share a single reservoir source. For instance, this may enable targeted delivery to multiple distinct locations. In a multi-lumen tube, each lumen may have its own valve. For the drug delivery application illustrated in FIG. 1, the valve 105 may be located at the tip of the tube 105 that is furthest from the drug reservoir 101. The valve may instead be placed anywhere else along the length of the tube.

Figure 2:
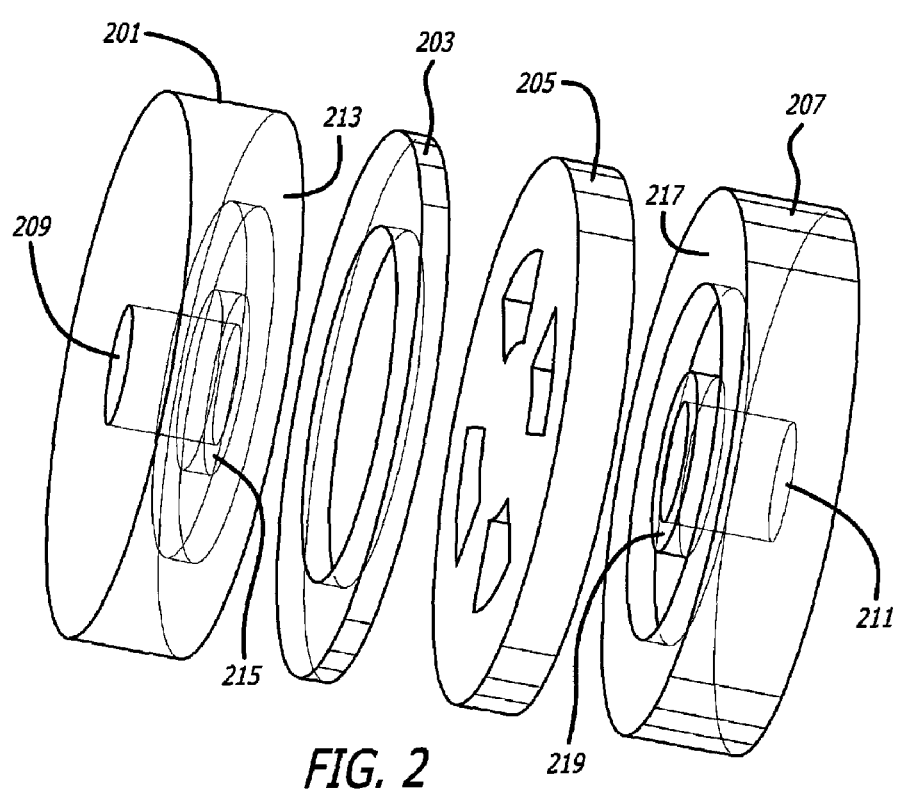
FIG. 2 is an exploded view of components of a valve illustrated in FIG. 1.

FIG. 2 is an exploded view of components of the valve 105 illustrated in FIG. 1. As illustrated in FIG. 2, the valve 105 may include four stacked disks: a pressure limiter 201, a spacer plate 203, a flexible valve plate 205, and a valve seat 207.

The valve 105 may have a pressure limiting feature packaged in round, medical grade heat-shrink tubing that may also serve as a tube through which the fluidic drug may be dispensed. The packaged valve may be easily integrated into an existing surgical model to help surgeons develop the process necessary to conduct ex vivo and in vivo experiments.

The pressure limiter 201 and the valve seat 207 may be identical or different in shape and/or size. Both may include a hole 209 and 211 through its respective center which may have any diameter, such as 200 μm, along with two raised rings 213, 215, 217, and 219. The inner raised ring 219 may be configured to enhance sealing between the valve seat 207 and the valve plate 205 which may be made of a silicone membrane. The outer rings 213 and 217 may be configured to clamp the spacer plate 203 and the valve plate 205 together so as to form a sandwiched stack of the four illustrated components.

Figure 3A:
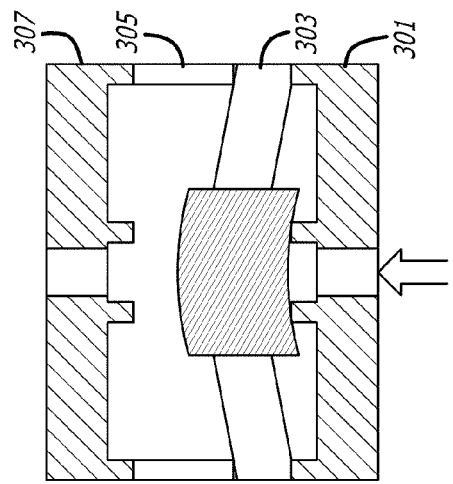
FIGS. 3(a)-3(c) Illustrate an example of valve operation.
Figure 3B:
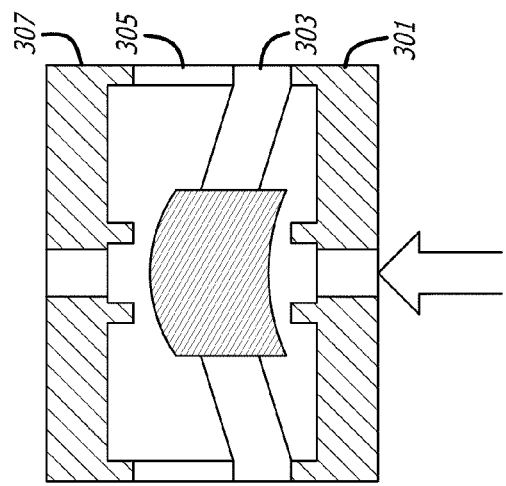
Figure 3C:
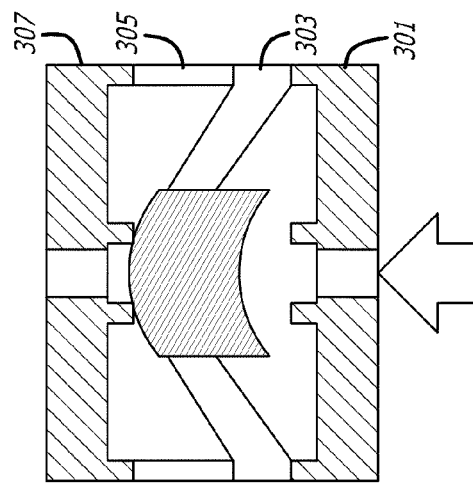

FIGS. 3(a)-3(c) Illustrate an example of valve operation. FIG. 3(a) illustrates the valve 105 closed under reverse pressure or small forward pressures. FIG. 3(b) illustrates applied forward pressure that exceeds valve cracking pressure, causing the valve 105 to open. FIG. 3(c) illustrates a large forward pressure that exceeds the closing pressure, causing the valve 105 to close.

The valve 105 may operate as a bandpass filter by allowing forward flow when the valve cracking pressure is exceeded. Flow may cease when the closing pressure is reached. The thickness of the spacer plate 203 may define the distance between the movable valve plate 205 and the pressure limiter 201. Its thickness may therefore set the closing pressure.

Additional disks may be used to add further features or to modify the operational parameters of the basic unit. For example, an additional spacer disk may be added to increase the pressure at which shut off occurs. The valve seat opening dimensions may be altered to create a normally-closed valve without bandpass regulation.

Figures 4, 5:
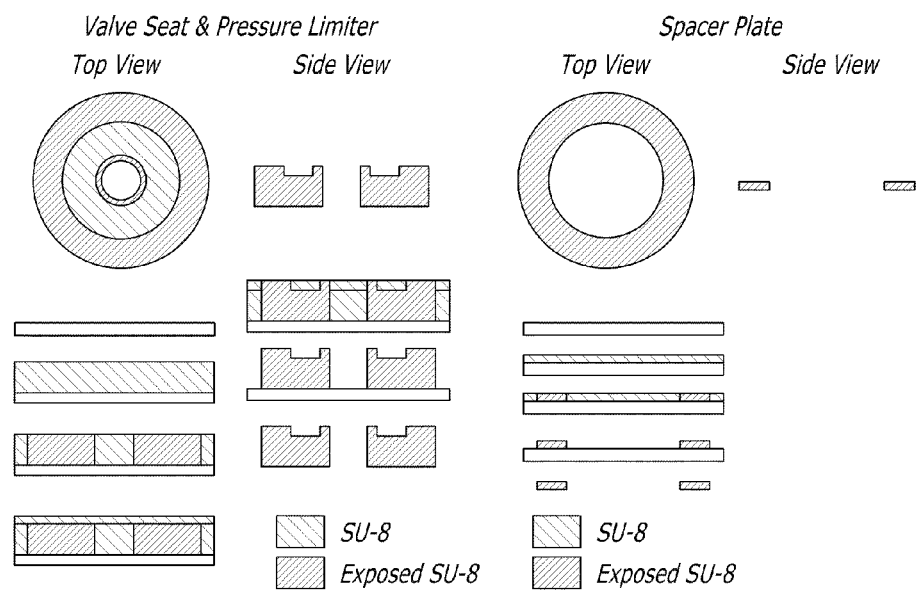
FIG. 4 illustrates three different valve plate designs (hole, arm, s-shape) that may be incorporated into a valve, along with other valve components and example dimensions.
FIG. 5 illustrates fabrication steps that may be taken to create a valve seat, a pressure limiter, and a spacer plate.

FIG. 4 illustrates three different valve plate designs (hole, arm, S-shape) that may be incorporated into the valve plate 205, along with other components and example dimensions. As reflected in FIG. 3, the valve plate 205 may have different designs (hole, arm, S-shape). Each different design may have different deflection and fluid resistance properties. All three designs may be evaluated and compared in order to determine the most suitable geometry for a particular drug delivery device application. Polymer materials may be chosen for their low Young's modulus and biocompatible properties. Other polymers and even metals may be used to modify the mechanical performance of the valve to suit a particular application.

FIG. 5 illustrates fabrication steps that may be taken to create the pressure limiter 201, the spacer plate 203 and the valve plate 205. These pieces may be made from SU-8, a light, curable epoxy-based polymer. When made from SU-8, these pieces may be fabricated on a soda-lime wafer and then released. The SU-8 pieces may be fabricated using standard techniques for single (spacer plate) or multiple layer (valve seat and pressure limiter) SU-8 structures. To fabricate the valve seat 207 and the pressure limiter 201, metal alignment marks may be processed onto a soda lime wafer using liftoff fabrication. The alignment marks may help prevent misalignment of features in each layer. Next, the wafer may be coated with a layer of OmniCoat (3 krpm, 30 sec) and then baked for 1 minute at 200° C. The OmniCoat processing step may be repeated twice for a total of three layers. OmniCoat may be used to help release the SU-8 structure from the soda lime substrate. Next, a layer of SU-8 2100 may be spun onto the surface (160 μm, 17500 rpm, 30 sec). The SU-8 layer may then be left at room temperature for 2 hours to improve SU-8 planarization. The structure may then be softbaked by slowly ramping (3° C./min) the substrate from room temperature to 95° C. The substrate may be baked at 95° C. for 2 hours before ramping back down to room temperature at 3° C./min. The SU-8 may then be exposed to a UV energy dose of 390 mJ/cm$^2$. Next, the system may be post exposure baked at 95° C. for 12 minutes. Again, the temperature may be ramped up and down from/to room temperature at a rate of at 3° C./min. Next a 40 μm layer of SU-8 2050 may be added to create the raised rings (4 krpm, 30 sec). Again, the structure may be left at room temperature for 1 hour to allow the SU-8 to planarize. This layer may be softbaked for 3 hours at 95° C. (3° C./min ramping rate), and then cooled at 3° C./min to room temperature. This layer may then be exposed (192 mJ/cm$^2$) and post-exposure backed for 14 minutes at 95° C. (increasing and decreasing temperature at 3° C./min). Finally, the SU-8 may be developed to reveal the SU-8 structures. The SU-8 structures may then be released by submerging the substrate in at 40° C. bath of Remover PG. The individual SU-8 pieces may then be rinsed with isopropyl alcohol and DI water.

The SU-8 spacer plate 203 may also be fabricated on soda lime wafers with metal alignment marks. OmniCoat may be applied to the substrate using the same recipe as for the valve seat 207 and the pressure limiter 201 described above. Next, SU-8 2050 may be spun onto the substrate (40 μm, 4 krpm, 30 sec) and softbaked for 1 hour at 95° C. (3° C./min temperature change). The SU-8 may be then exposed to 240 mJ/cm$^2$ and post-exposure baked for 6 minutes at 95° C. (3° C./min ramping). The SU-8 spacer plates may be developed, rinsed, and released using the same steps as outlined for the valve seat and pressure limiter.

The SU-8 pieces may be hardbaked at 220° C. (again, ramping from room temperature to 220° C. at a rate of 3° C./min, and cooled to room temperature at a rate of 3° C./min). The hardbake process may be necessary to ensure the SU-8 pieces can survive the packaging step.

Figure 6:
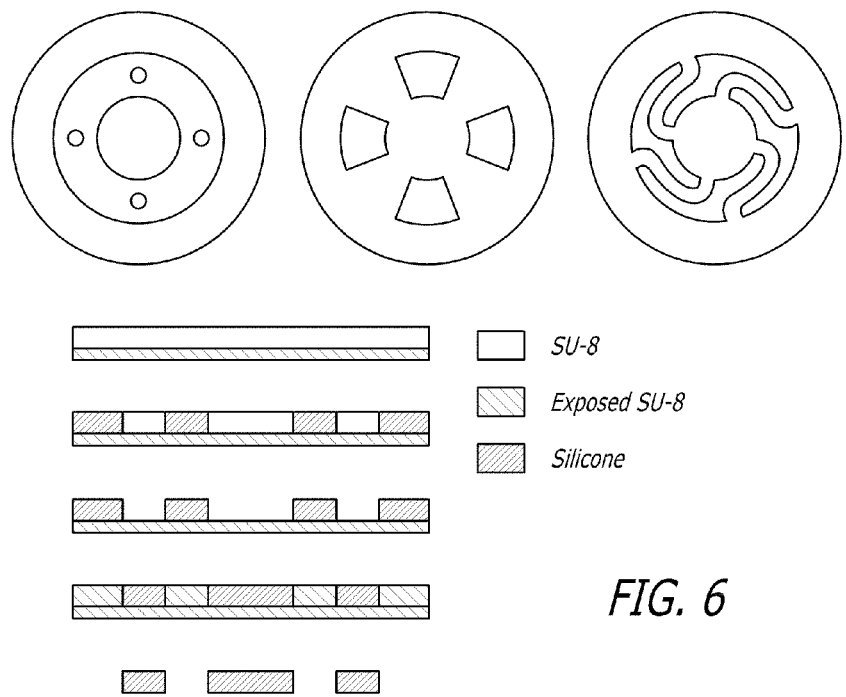
FIG. 6 illustrates a fabrication step that may be used to make valve plate replicas utilizing SU-8 molds.

FIG. 6 illustrates a fabrication step that may be taken to make valve plate replicas utilizing SU-8 molds. The movable valve plates may be fabricated from medical grade silicone rubber (MDX4-4210) in SU-8 molds. The SU-8 molds may be filled with MDX4-4210 and placed into a vacuum oven to remove the bubbles from the silicone prepolymer. Once the bubbles are removed, excess silicone may be removed by slowly scraping the top of the mold. The silicone may then be cured at room temperature (approximately 24 hours). The silicone may then be removed from the mold. The replicas may be examined under a microscope. Any extra silicone may be carefully removed so that the final valve plate has a circular shape and the membrane holes are unobstructed.

Figure 7:
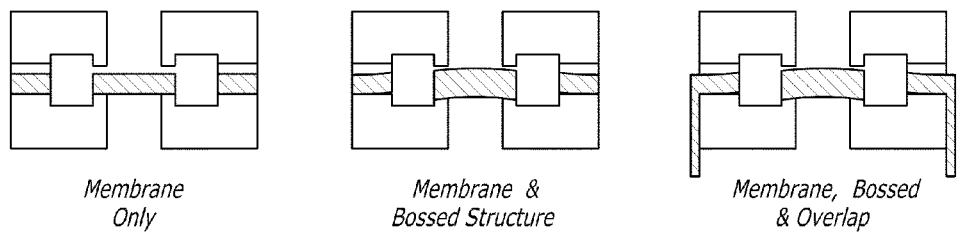
FIG. 7 illustrates how valve plates may be altered to enhance basic valve design.

FIG. 7 illustrates how valve plates may be altered to enhance the basic valve design. As illustrated in FIG. 7, additional features may be added to the valve plate. Bossed structures may be added to create a greater seal between the valve seats and valve plates. Overhang structures may be added on the valve plate to enclose the valve seat and facilitate packaging.

Figure 8:
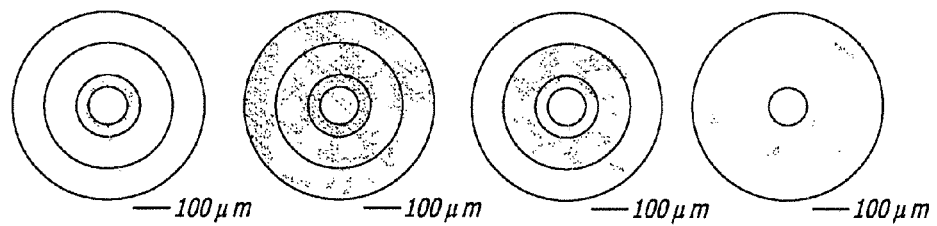
FIG. 8 are images that show stacking of a valve seat, valve plate, spacer plate, and a pressure limiter.

FIG. 8 are images which show stacking of the valve seat, valve plate, spacer plate and the pressure limiter.

Figure 9:
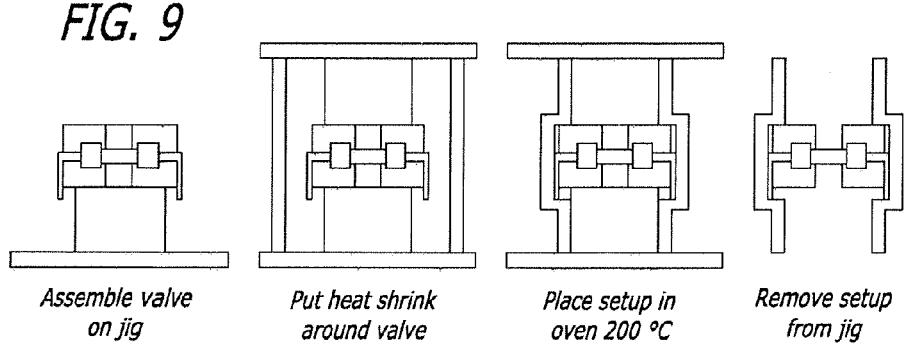
FIG. 9 Illustrate packaging steps that may be used to encase a valve in a heat shrink tube.

FIG. 9 Illustrate packaging steps to encase the valve in a heat shrink tube. The valve may instead be press fitted into the tube.

Figure 10:
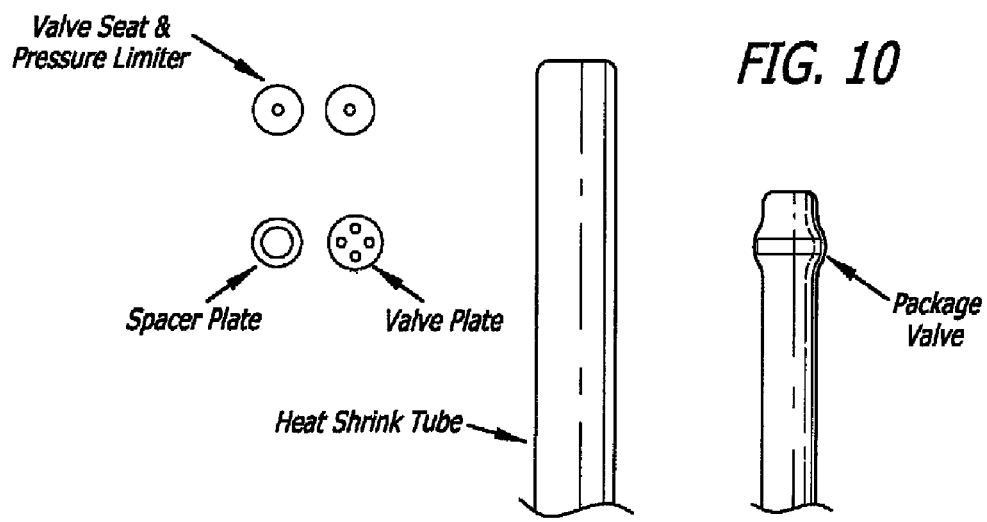
FIG. 10 is a photograph of valve components (valve seat, valve plate, spacer plate, and pressure limiter), a heat-shrink tube, and a fully assembled valve.

FIG. 10 is a photograph of valve components (valve seat, valve plate, spacer plate, and pressure limiter), a heat-shrink tube, and a fully assembled valve. Ruler divisions measure 1 mm.

Figure 11:
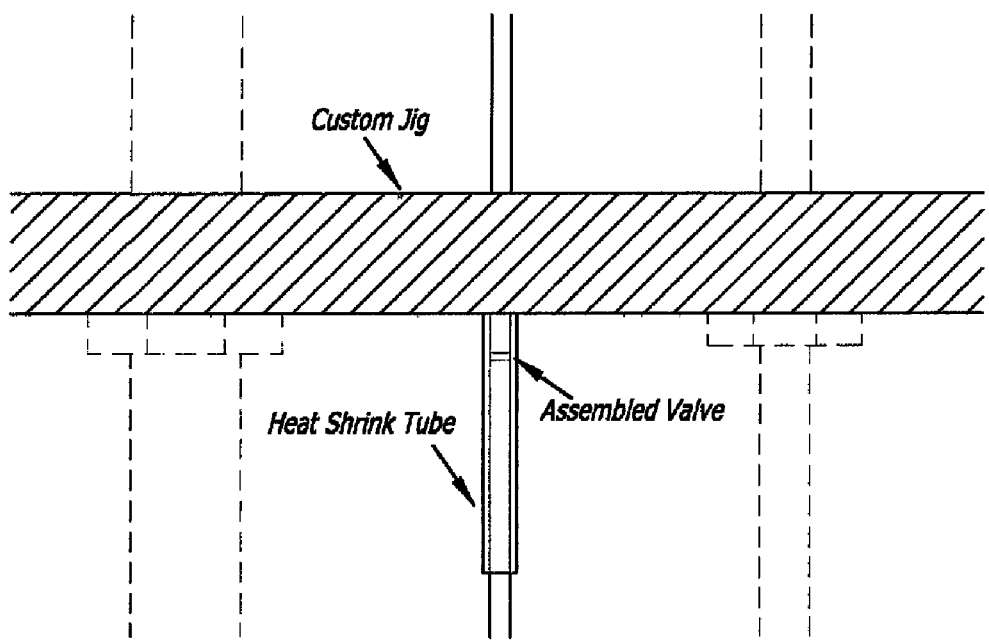
FIG. 11 is an image of a jig that may be used to package a valve.

FIG. 11 is an image of a jig which may be used to package a valve. Individual valve components may be aligned and then placed into the jig. The heat-shrink tube may be placed around the stack. The jig may be used to keep the valve components flush against each other and perpendicular to the tube. The entire jig may be placed into an oven for controlled heating and cooling in order to produce uniform shrinkage of the tube around the valve.

Individual pieces of the valve (valve seat, valve plate, spacer plate, pressure limiter) may be stacked together and packaged into a biocompatible 22G fluorinated ethylene propylene (FEP) heat-shrink tube. Other heat shrink materials may be used, but FEP may be chosen for this application because SU-8 may be highly temperature sensitive and FEP may have a lower shrink temperature than the other materials. The circular tube may facilitate ocular tissue/tube conformation.

Figure 12:
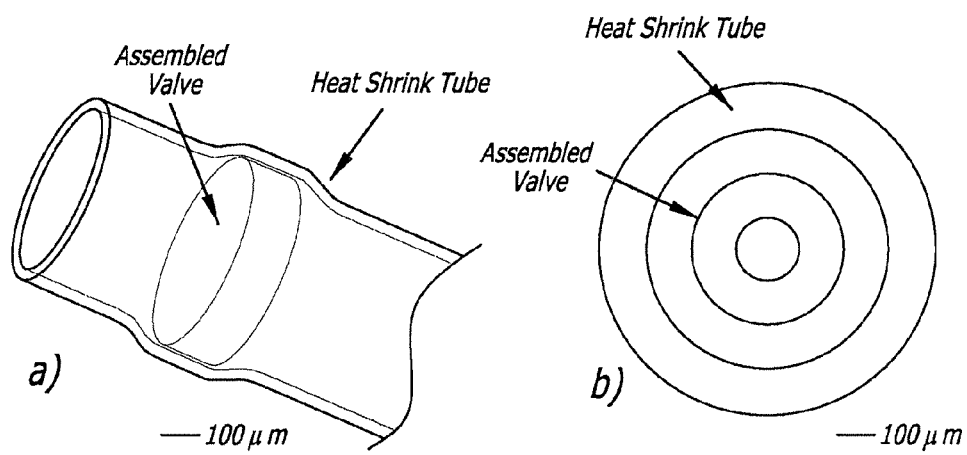
FIG. 12(a) is a side view and FIG. 12(b) is a top view of a packaged valve in an FEP heat-shrink tube.

FIG. 12(*a*) is a side view and FIG. 12(*b*) is a top view of a packaged valve in an FEP heat-shrink tube. The valve may be placed inside the tube utilizing a custom-made jig and then heated to 215° C. at 1.5° C./min, and cooled at the same rate to room temperature.

EXPERIMENTAL SETUP AND RESULTS

Packaging Leakage or Burst Pressure

A solid SU-8 disc with the same diameter as the valve was packaged in heat-shrink tubing and pressurized. The disc remained stable and the entire system was leak-tight up to 2000 mmHg (266.6 kPa) which is the pressure limit of the testing apparatus. This packaging method may be extremely robust and may not require any adhesives.

Membrane Deflection

Figure 13:
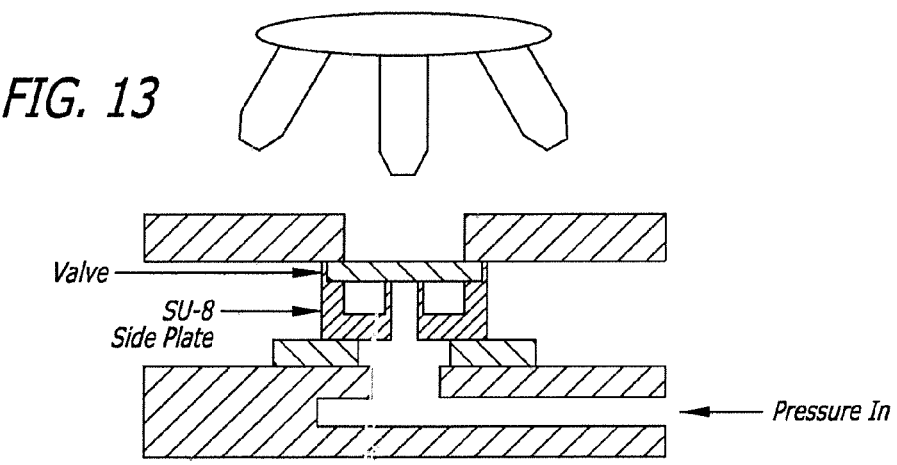
FIG. 13 illustrates a jig setup used to obtain valve plate deflection data.

FIG. 13 illustrates a jig setup used to obtain the valve plate deflection data. As illustrated in FIG. 13, individual valve plates were stacked on a valve seat and clamped into a custom-made jig. The jig was then placed under a microscope and attached to a pressure system. The initial valve plate position was recorded by reading the tick mark on the calibrated focus knob on the microscope (separated by 1 μm increments). Pressurized air was then applied to the membrane in predetermined increments (10, 25, 50, 75, 100, 200, 300, 400, 500 mmHg). The microscope was refocused and the new knob position was recorded. The amount of membrane deflection was calculated based on difference between the initial and final focus position.

The experimentally obtained results were compared with the theoretical relationship using the large deflection equations for a clamped membrane of uniform thickness where maximum deflection ($w_{max}$) was calculated from membrane thickness (t), applied pressure (p), membrane radius (a), Young's Modulus (E), and Poisson's Ratio (v) See A. C. Ugural, *Stresses in Plates and Shells,* 2nd ed., (McGraw-Hill, 1999), pp. 305-318.

Finite-element models (FEM) were constructed to simulate valve performance. Valve plate deflections as well as stress information were obtained from FEM analyses.

Figure 14:
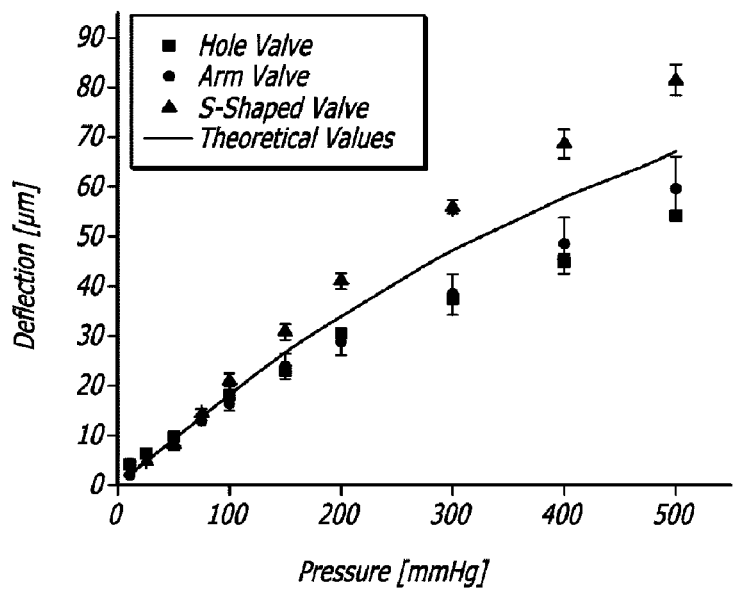
FIG. 14 illustrates a comparison of calculated valve deflection values using theoretical equations to experimentally obtained values for the three designs illustrated in FIG. 10.

FIG. 14 illustrates a comparison of calculated valve deflection values using theoretical equations to experimentally obtained values for all three designs (n=4, Mean±SE). As expected, the hole and arm valves had similar performance and the s-shaped valve had the greatest deflection.

Figure 15A:
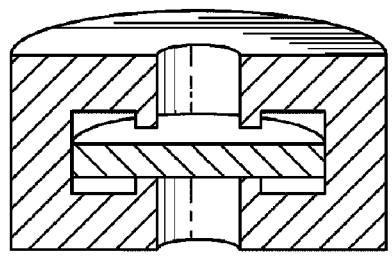
FIGS. 15(a)-15(d) illustrate FEM images of deflection of a valve plate under various pressures.
Figure 15B:
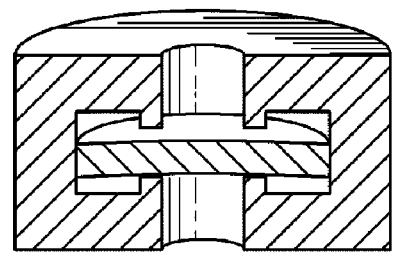
Figure 15C:
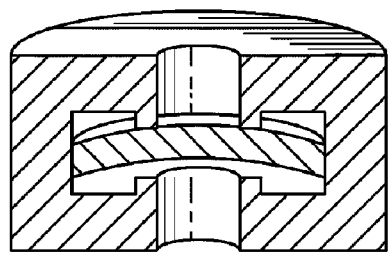
Figure 15D:
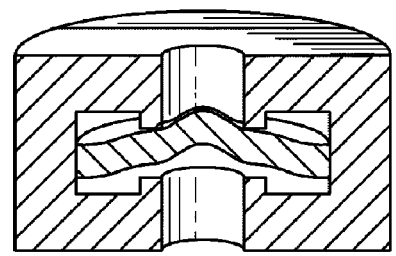

FIGS. 15(a)-15(d) illustrate FEM images of deflection of the valve plate under various pressures. FIG. 15(a) illustrates the deflection under negligible forward pressure; FIG. 15(b) under 100 mmHg; FIG. 15(c) under 500 mmHg; and FIG. 15(d) under 10000 mmHg (used to amplify the illustration of how the valve closes). Forces between the valve seat and valve plate were not modeled; therefore, the valve opened for any non-zero applied forward pressure.

Figure 16:
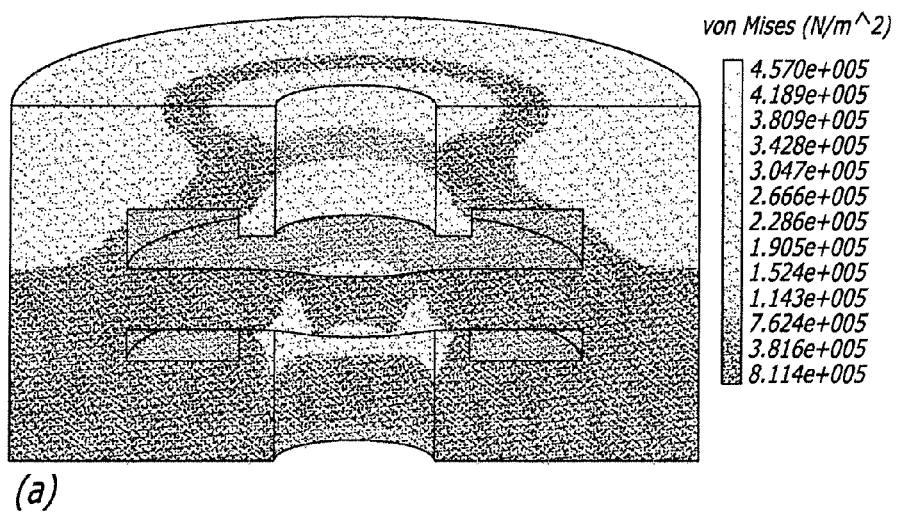
FIGS. 16(a)-16(b) illustrate FEM analysis of 500 mmHg reverse pressure on an assembled valve.
Figure 16:
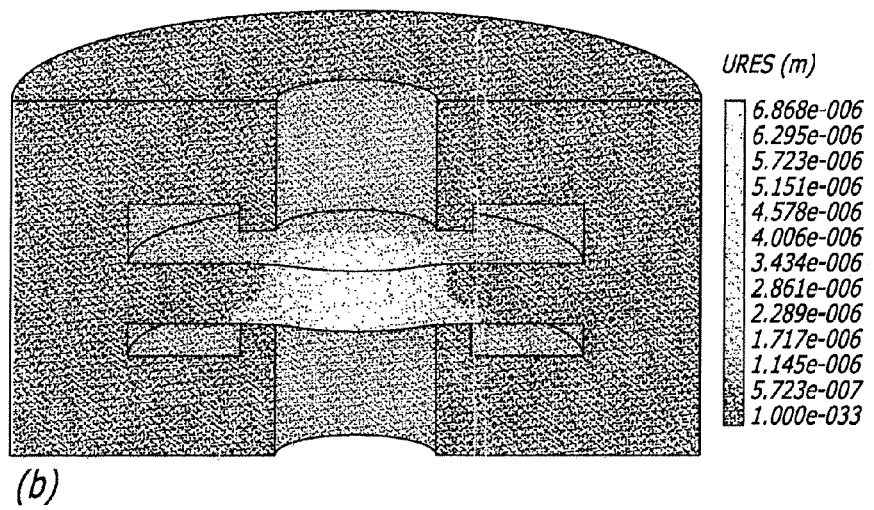

FIGS. 16(a)-16(b) illustrate FEM analysis of 500 mmHg reverse pressure on the assembled valve. FIG. 16(a) illustrates stress (0.246 MPa) much lower than the tensile stress of the valve plate (MDX4-4210, 5 MPa) or the pressure limiter (SU-8, 60 MPa). FIG. 16(b) illustrates that deflection of the valve plate was less than 7 μm.

FEM analysis shows the stages of valve operation shown in FIGS. 15(a)-15(d) and FIGS. 16(a)-16(b). Under forward applied pressure (1000 mmHg), the maximum stress on the valve plate was <75% of MDX4-4210 tensile strength (5 MPa). Reverse pressure analysis verified the stress on the valve (0.457 MPa) was less than the tensile stress valve material.

Valve Flow Rate

Figure 17:
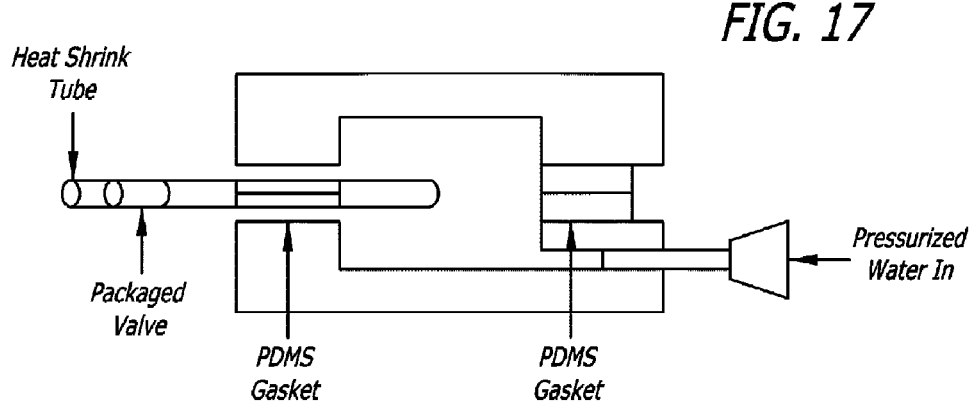
FIG. 17 illustrates a custom-made jig to test cracking pressure, closing pressure, and flow rate of packaged check valves.

FIG. 17 illustrates a custom-made jig to test cracking pressure, closing pressure, and flow rate of the packaged check valves. The heat-shrink tube was clamped into the jig, and pressurized water was introduced to the jig via a syringe needle. The outlet of the tube was connected to a calibrated pipette. Valve properties were calculated based on water flow in the pipette.

As illustrated in FIG. 17, a packaged valve was clamped into a custom-made jig in order to obtain the cracking pressure, closing pressure, and flow rate through the valve. Pressurized water (0-1000 mmHg, 0-133.3 kPa) was applied and the flow rate was measured using a calibrated pipette.

Figure 18:
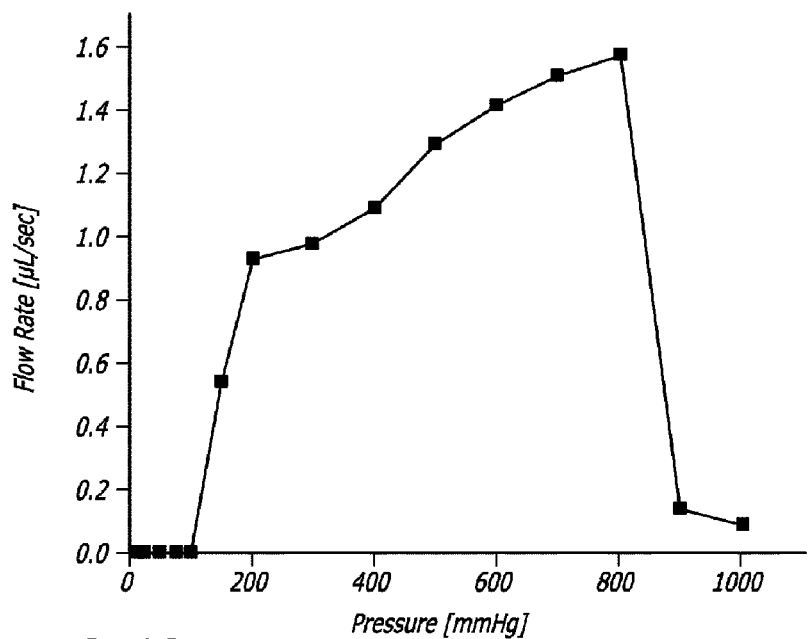
FIG. 18 illustrates bandpass regulation of fluid flow verified on a packaged valve.

FIG. 18 illustrates bandpass regulation of fluid flow verified on a packaged valve. DI water was applied to the inlet of a package hole valve and the corresponding flow rate was measured using a 100 μL calibrated pipette. The thickness of the valve seat was 62 μm.

As illustrated in FIG. 18, preliminary data indicates a cracking pressure of 150 mmHg and a closing pressure of 900 mmHg for the hole valve plate design where the valve plate is 62 μm thick. A second hole valve with a thicker valve plate (t=101 μm) was able to demonstrate bandpass regulation of fluid flow for 3 repeated trials. However, flow rate through the valve decreased for each subsequent run.

Figure 19:
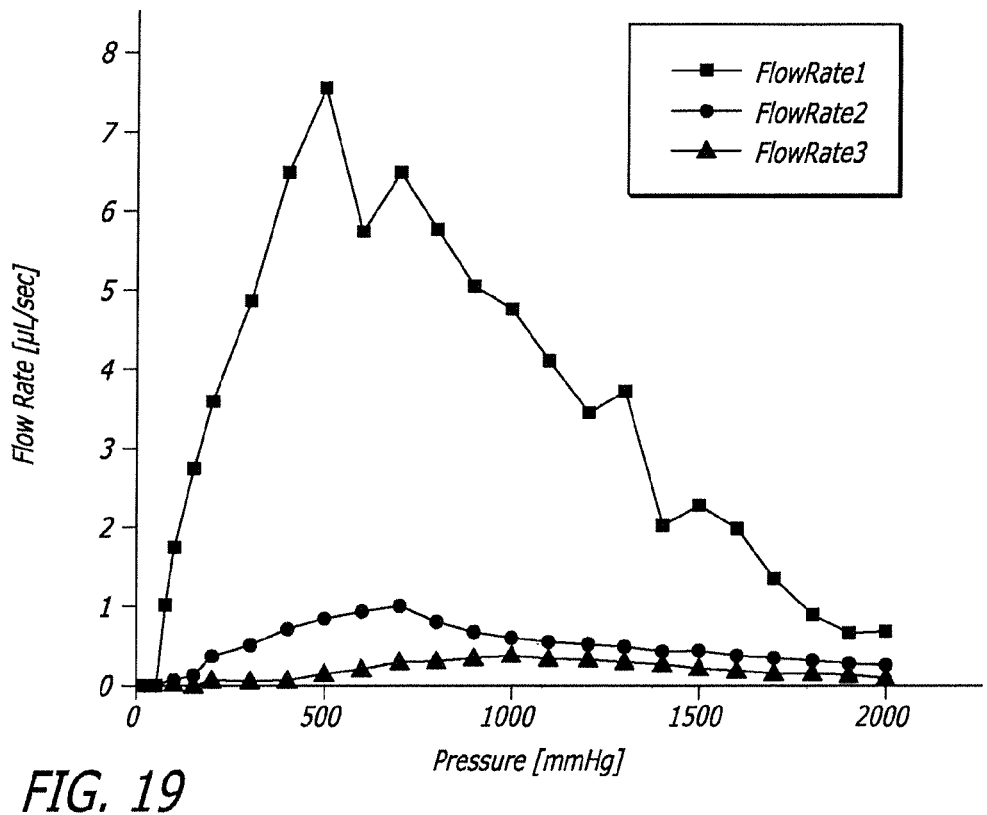
FIG. 19 illustrates a second valve exhibiting bandpass regulation of fluid flow.

FIG. 19 illustrates a second valve exhibiting bandpass regulation of fluid flow. DI water was applied to the inlet of a package hole valve and the corresponding flow rate was measured using a 100 μL calibrated pipette. The valve was pressurized 3 times to determine repeatability of regulation. The valve demonstrated regulation in all three runs; however, the flow rate diminished during subsequent trials. The thickness of the valve seat was 101 μm.

The decrease in flow rate may be due in part to fouling of the valve where the valve becomes blocked by particulates in the water. A minimal leakage less than 18× peak flow was observed after valve closure. The valve was able to withstand reverse pressure in excess of 500 mmHg.

Figure 20:
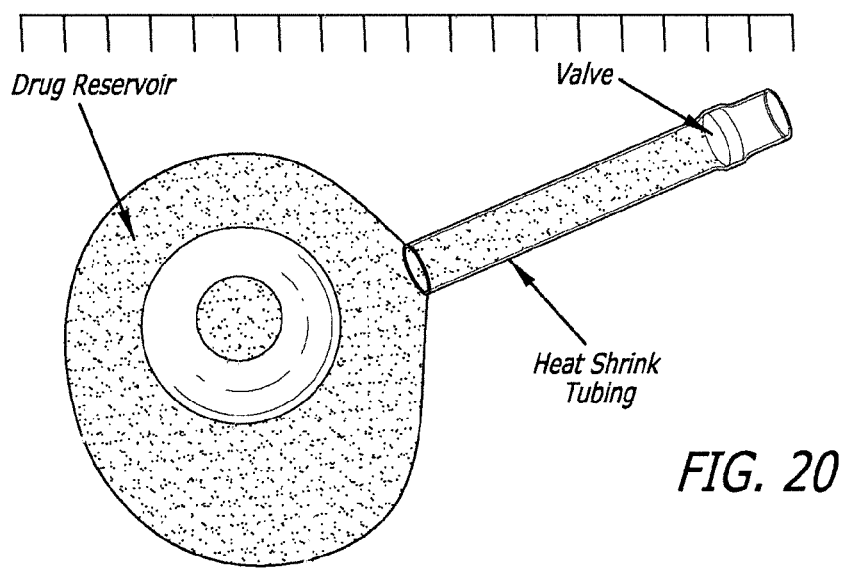
FIG. 20 illustrates a packaged valve incorporated into a surgical model for in vivo testing.

FIG. 20 illustrates a packaged valve incorporated into surgical model for in vivo testing. The packaged valve may be easily exchanged for another packaged valve, providing a modular design and rapid prototyping. Ruler divisions measure 1 mm.

The valve may be designed to be used in an ocular drug delivery device. The valve may be incorporated into a surgical model of the drug delivery device (made of silicone rubber) that may be used for ex vivo and in vivo testing, as illustrated in FIG. 20. The valve's modular design may permit the valve sections to be easily replaced or exchanged to create a valve suitable for other applications. Additionally, fully packaged valves may be treated as components that can be incorporated into devices without having to be fabricated together.

Preliminary testing on the valve has demonstrated that the valve may be encased in a robust package without the need for adhesives. Different valve plate designs were created to demonstrate how valve plate geometry affects valve performance. Theoretical and FEM models were used to verify empirically obtained data. The valve may provide a bandpass regulation of fluid flow, where flow can be achieved when the applied pressure is greater than the cracking pressure (e.g., 150 mmHg) but less than the closing pressure (e.g., 900 mmHg). The valve components may be made from FDA class VI approved material (if available) in order to create a valve that may be incorporated into medical devices.

The components, steps, features, objects, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

For example, additional spacer plates may be added to further adjust the closing pressure; the pressure limiter plate may be modified to create a normally-closed valve without bandpass regulation; the annular protrusions in the valve seats may be substituted with other mechanical sealing structures; and the flexible arms in the valve plate may be modified to increase or decrease the overall stiffness of the plate, thus modifying the valve's overall fluidic performance.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases in a claim mean that the claim is not intended to and should not be interpreted to be limited to any of the corresponding structures, materials, or acts or to their equivalents.

Nothing that has been stated or illustrated is intended or should be interpreted to cause a dedication of any component, step, feature, object, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

The invention claimed is:

1. A drug delivery device comprising:
a drug reservoir configured to contain and controllably deliver a fluidic drug;
a tube configured to deliver the fluid from the drug reservoir through a lumen in the tube to another location, the lumen in the tube having a diameter that is no more than 900 µm; and
a valve wholly within the lumen of the tube which regulates the flow of the fluid through the tube without substantially diverting the direction in which the fluid flows through the tube and without causing the diameter of the portion of the tube that surrounds the valve to increase substantially.

2. The drug delivery device of claim 1 wherein the valve includes a valve seat and a flexible valve plate configured to rest against the valve seat, both of which contain at least one fluid-communication channel in line with the lumen of the tube.

3. The drug delivery device of claim 2 wherein the valve plate includes a plurality of fluid-communication channels in line with the lumen of the tube.

4. The drug delivery device of claim 3 wherein each fluid-communication channel in the valve plate has a cross section that is substantially circular.

5. The drug delivery device of claim 3 wherein each fluid-communication channel in the valve plate has a cross section that is substantially S-shaped.

6. The drug delivery device of claim 3 wherein each fluid-communication channel in the valve plate has a cross section that is substantially polygonal.

7. The drug delivery device of claim 1 wherein the valve contains only a single member which moves during operation of the valve.

8. The drug delivery device of claim 1 wherein the valve is configured to regulate the flow of fluid in a bandpass manner by allowing fluid to flow through the valve only when the pressure of the fluid is above a minimum and below a maximum.

9. The drug delivery device of claim 1 wherein the valve is held in place within the tube solely by frictional force between the valve and a wall of the tube.

10. A drug delivery device comprising:
a drug reservoir configured to contain and controllably deliver a fluidic drug;
a tube configured to deliver the fluid from the drug reservoir through a lumen in the tube to another location; and
a valve having only a single member which moves during operation of the valve and which is configured to regulate the flow of the fluid through the tube in a bandpass manner by allowing fluid to flow through the valve only when the pressure of the fluid is above a minimum and below a maximum.

11. The drug delivery device of claim 10 wherein the single member is a flexible valve plate and wherein the valve includes a pressure limiter, a valve seat, and a spacer between the flexible valve plate and the pressure limiter.

12. The drug delivery device of claim 11 wherein the valve is configured such only the valve plate moves during operation of the valve.

13. The drug delivery device of claim 11 wherein the pressure limiter and the valve seat each include an annular protrusion.

14. The drug delivery device of claim 13 wherein the pressure limiter and the valve seat each include two, separated annular protrusions.

15. The drug delivery device of claim 14 wherein each of the two annular protrusions are concentric.

16. The drug delivery device of claim 10 wherein the valve is held in place within the tube solely by frictional force between the valve and a wall of the tube.

17. A drug delivery device comprising:
a drug reservoir configured to contain and controllably deliver a fluidic drug;
a tube configured to deliver the fluid from the drug reservoir through a lumen in the tube to another location; and
a valve configured to regulate the flow of the fluid through the tube which is held in place within the tube solely by frictional force between the valve and a wall of the tube, the valve having components that are held in place with respect to one another solely by the frictional force between the valve and the wall of the tube.

18. The drug delivery device of claim 17 wherein the valve includes a stack of disk-like components held together solely by the frictional force.

19. The drug delivery device of claim 17 wherein the frictional force is the result of shrinkage of the tube wall surrounding the valve after the valve was placed within the lumen of the tube.

20. The drug delivery device of claim 19 wherein the shrinkage was caused by application of heat to the tube.

21. The drug delivery device of claim 17 wherein the frictional force is the result of the valve having been press fitted within the lumen of the tube.

* * * * *